(12) United States Patent
McDonald et al.

(10) Patent No.: US 6,595,207 B1
(45) Date of Patent: Jul. 22, 2003

(54) OXYGEN DIFFUSER FOR PATIENT OXYGEN DELIVERY SYSTEM

(75) Inventors: Lee McDonald, Barrie (CA); Maurice Lavimodiere, Barrie (CA)

(73) Assignee: Southmedic Incorporated, Ontario (CA)

( * ) Notice: Subject to any disclaimer, the term of this patent is extended or adjusted under 35 U.S.C. 154(b) by 124 days.

(21) Appl. No.: 09/659,503

(22) Filed: Sep. 11, 2000

(51) Int. Cl.[7] ............................................. A62B 29/00
(52) U.S. Cl. ........................... 128/200.28; 128/200.24; 128/206.27; 128/207.11
(58) Field of Search .................. 128/200.28, 201.24, 128/207.17, 207.18, 201.19, 200.27, 204.23, 200.18, 205.11, 205.25, 204.24, 204.25, 203.29, 204.11, 204.12

(56) References Cited

U.S. PATENT DOCUMENTS

| | | | |
|---|---|---|---|
| 1,974,828 A | | 9/1934 | Markut |
| 2,906,463 A | * | 9/1959 | Curry ..................... 128/200.21 |
| 3,040,741 A | | 6/1962 | Carolan |
| 3,522,806 A | * | 8/1970 | Szekely ................. 128/200.18 |
| 3,683,907 A | | 8/1972 | Cotabish |
| 3,850,168 A | | 11/1974 | Ferguson |
| 3,963,021 A | * | 6/1976 | Bancroft ................ 128/201.25 |
| 4,739,757 A | | 4/1988 | Edwards |
| 5,104,430 A | * | 4/1992 | Her-Mou ................ 128/205.29 |
| 5,697,363 A | * | 12/1997 | Hart ....................... 128/201.19 |
| 6,065,473 A | * | 5/2000 | McCombs et al. ..... 128/200.24 |
| 6,247,470 B1 | * | 6/2001 | Ketchedjian ........... 128/200.28 |

FOREIGN PATENT DOCUMENTS

| | | | |
|---|---|---|---|
| CA | 1128826 | 8/1982 | .................. 128/66 |
| CA | 2251531 | 4/1997 | |
| WO | WO 97/38746 | 10/1997 | .......... A61M/16/00 |
| WO | WO 99/13929 | 3/1999 | .......... A61M/10/00 |

* cited by examiner

*Primary Examiner*—Weilun Lo
*Assistant Examiner*—Mital Patel
(74) *Attorney, Agent, or Firm*—Thomas J. Nikolai; Nikolai & Mersereau, P.A.

(57) ABSTRACT

An oxygen diffuser for a lightweight oxygen delivery system for a patient, the oxygen delivery system being of the type comprising a mount for seated engagement on a patient's head or ear, an elongated tubular boom for oxygen delivery secured at one end to the mount and having the diffuser secured to the other end, the diffuser to deliver oxygen passed through the boom to a space in the vicinity of the patient's nose and mouth, the diffuser comprising a body having a wall, the interior surface of which wall is of generally concave configuration, circumscribing a centrally positioned oxygen outlet so as to direct the flow of oxygen from the outlet generally towards the patient's nose and mouth; and a baffle seated over the oxygen outlet so as to assist in mixing of oxygen with ambient air and avoid a direct flow of oxygen towards the patient's face.

10 Claims, 4 Drawing Sheets

OXYGEN DIFFUSER FOR PATIENT OXYGEN DELIVERY SYSTEM

BACKGROUND OF THE INVENTION

The present invention relates to a novel system for delivery of oxygen to a patient, and more particularly to a system which can be used to replace conventional oxygen masks and nose cannula oxygen delivery systems.

Mask oxygen therapy has been around for a very long time and has seen virtually no changes. Problems encountered with this style of therapy are well known but unavoidable using the mask as it is supplied today. A number of vendors supply oxygen masks as a commodity item, with the result that there has been little or no improvement in the technology because of the low profit margins accompanying the sale of such masks.

Conventional oxygen masks comprise tent-like structures which are strapped over the nose and mouth of the patient, often using an elastic band or bands behind the patient's ears or head. Oxygen is fed from a supply through a tube into the bottom portion of the mask at the front of the patient.

Common problems with the mask include:
1. Some patients find it claustrophobic.
2. Many patients cannot tolerate the smell of plastic resin.
3. Patients must take the mast off to speak or eat thereby discontinuing therapy.
4. Some patients are allergic to the elastic (latex allergy).
5. Some patients feel ill when they wear an oxygen mask, (the psychological effect is truly remarkable on the patient and the patient's family alike).
6. Patients often aspirate if they vomit while wearing the mask.
7. The mask cannot be used during facial surgery due to intrusions into the sterile field.
8. The mask cannot be worn if the patient has facial injuries such as burns.
9. Skin irritation is often found from the plastic.
10. The face mask does not effectively fit all sizes and shapes of face. Often the soft plastic masks are delivered in a deformed fashion.
11. The face mask usual necessitates clipping the oxygen delivery tube in front of the patient at the bottom of the mask. This is awkward and inconvenient as it may interfere with a patient's movement.
12. The face mask creates irregular infusion of oxygen by the patient, with exhaled air from the patient being mixed with oxygen in the mask.

Another current approach to oxygen delivery to a patient employs an oxygen delivery tube with tubular open ended nasal prongs or cannulae at the delivery end of the tube for insertion into a patient's nasal passages. Disadvantages of nasal cannulas include:
1. The patient may not be a nose breather.
2. Patents often get nose bleeds from the dryness of the nasal cannulas.
3. Patients find the front oxygen cord, necessary with nasal cannulas, difficult to handle as it hangs down directly in front of them and applies downward pressure on their ears, where the cord is again suspended, as in the case of masks.

Of background interest is U.S. Pat. No. 4,593,688 of Payton issued Jun. 10, 1986, which describes and illustrates a tubular system for, example, delivery nebulized oxygen enriched fog or the like to the face and mouth of a croup patient, the tube being suspended, at its delivery end, from a series of straps secured about a patient's head. A portion of the tube is mounted on a pivoting, u-shaped frame member so that the tubing is held in front of and below the patient's face, for delivery of the nebulized oxygen enriched fog. The gas delivery to the nose and mouth area of the patient is through orifices in the tube, near the patient's nose and mouth when the tube is in position. This system is intended for children, and would be uncomfortable and restrictive to one's movements, if placed in position on a patient for a long period of time.

Also of background interest is PCT application WO 99/13929 published Mar. 25, 1999 of Combs et al. This reference describes and illustrates an oxygen delivery system for non-medical uses, for instances in oxygen bars or for oxygen enhancing during exercises such as aerobics or weight lifting. The system comprises a re-usable headset and a conduit to direct oxygen from a source to a headset and to a region proximate to the user's nose and mouth. The conduit is supported by a delivery arm which is preset to a predetermined distance from a user's head for proper supply of oxygen to the user's nose and mouth area.

Also relevant is Knoch et al U.S. Pat. No. 5,575,282 issued Nov. 19,996, which describes and illustrates a distribution system oxygen to a patient's nose and mouth. This system includes a helix for mixing and spirally delivering oxygen towards the patient.

In co-pending application Ser. No. 09/572,637 filed May 17, 2000, there is described a lightweight oxygen delivery system for a patient comprising a headband or an ear support to be comfortably seatably engaged over a patient's head or ear. A clip is secured to the headband or ear support. An elongated tubular boom is secured at one end to the clip to extend and hold its position, when in operation from said one end at the clip to another end located at a space in front of, and proximal to the patient's nose and mouth. An oxygen diffuser is located at the other end of the boom, to deliver oxygen from the boom to the space in the vicinity of the patient's nose and mouth. The clip is constructed so as to hold securely an oxygen delivery tube from an oxygen source in fluid communication with the said one end of the boom so as to deliver oxygen from the source to the boom for discharge through the diffuser.

It is an object of the present invention to provide an oxygen diffuser for such a system.

The oxygen diffuser according to the present invention, as will be described in more detail subsequently, provides an effective and efficient manner of delivering oxygen to a patient, avoiding many of the problems inherent with conventional medical oxygen delivery systems such as face masks and nasal cannulae.

BRIEF DESCRIPTION OF THE DRAWINGS

These and other advantages of the invention will become apparent upon reading the following detailed description and upon referring to the drawings in which.

Figure 1:
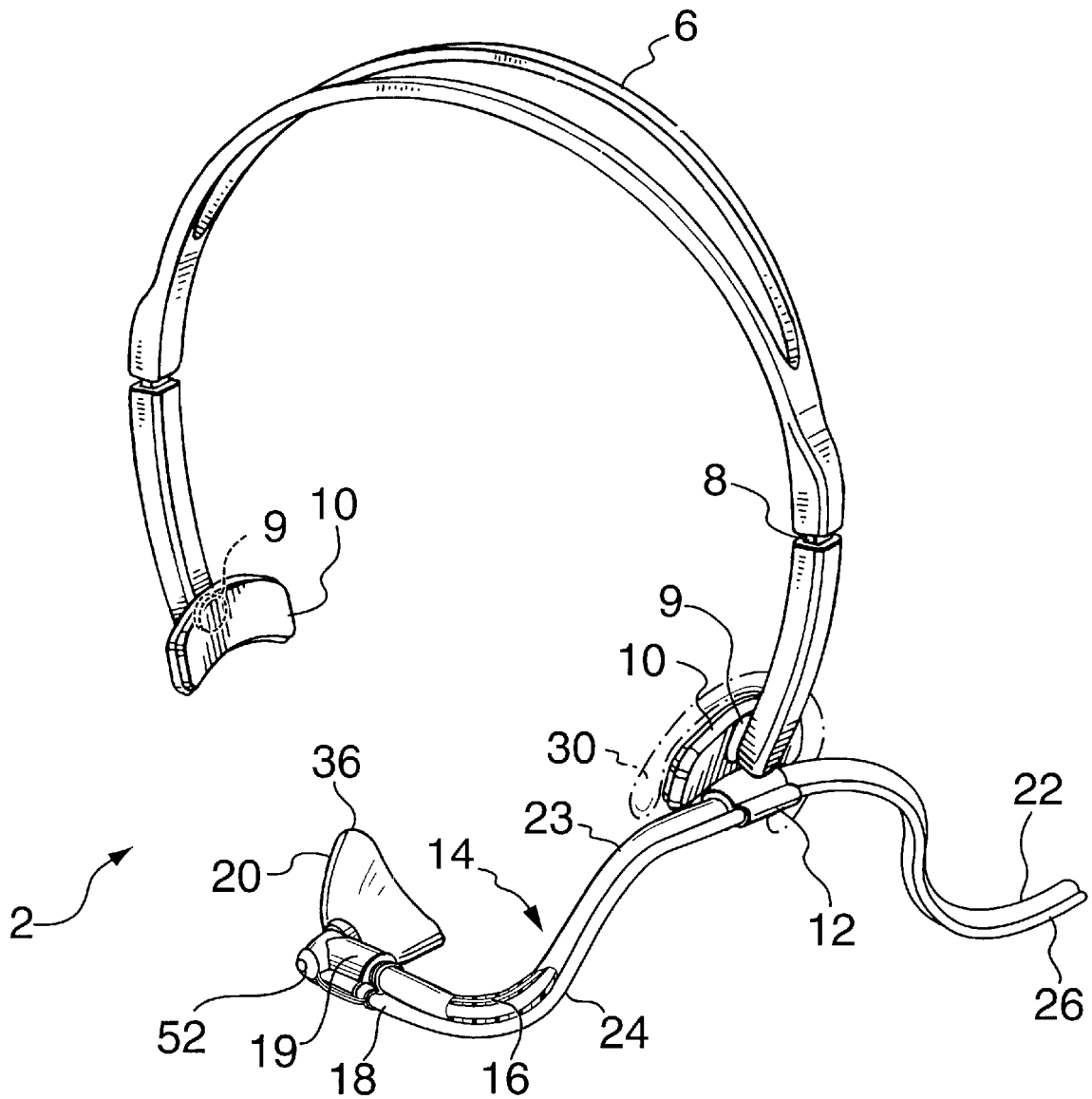
FIG. 1 is a perspective view of an oxygen delivery system according to the present invention mounted on the head of a patient.

While the invention will be described in conjunction with illustrated embodiments, it will be understood that it is not intended to limit the invention to such embodiments. On the contrary, it is intended to cover all alternatives, modifications and equivalents as may be included within the spirit and scope of the invention as defined by the appended claims.

DETAILED DESCRIPTION OF THE PREFERRED EMBODIMENTS

In the following description, similar features in the drawings have been given similar reference numerals.

Turning to FIG. 1, there is shown a lightweight delivery system 2, in accordance with the invention, to be mounted on the head of a patient. The system comprises a curved resilient headband 6 which is provided with suitable adjustment means such as telescopic portions 8 and swivel connections 9, to enable the headband to be seated comfortably, from side to side over or behind the patient's head (or in positions therebetween or reversed thereon). A pair of soft pads 10, made of rubber or other suitable material, are secured to swivel connections 9 and to the insides of the end portions of headband 6. To one side of headband 6 is secured a clip 12, which in the illustrated embodiment is of sleeve-like configuration. Secured to clip 12 is a tubular boom 14 which extends downwardly and forwardly to end at a space in the vicinity of the patient's nose and mouth. Boom 14 is preferably a plastic tube in which is embedded a positioning wire 16 which enables the tube to be bent into an appropriate shape to position the lower end 18 of boom 14 as required for delivery of oxygen to the patient, and to be held in that position.

At this lower end 18 of boom 14 is a fastener 19 to which is secured an oxygen diffuser 20 through which oxygen, fed into boom 14, is passed into the space in front of the patient's nose and mouth. The boom construction of the system according to the present invention enables adjustment from left to right and from front to back and for reversal of the headband's seating on different patient's heads (i.e. so the boom is positioned on either the left or the right side), for precise oxygen delivery. The key is that the diffuser 20, regardless of how headband 6 is seated on a patient's head, preferably sits centrally approximately one half inch from the patient's mouth and nose. Diffuser 20 allows for the administration of the oxygen flow to the patient without the patient feeling a direct flow of air onto his/her face. From an appropriate oxygen source (not illustrated) an oxygen delivery tube 22 extends to and is releasably engaged in the sleeve of clip 12 for fluid communication with the tubular boom 14. In this manner clip 12 provides for oxygen delivery from tube 22 to boom 14 and diffuser 20.

While boom 14 may consist solely of a single plastic tube 23, specifically designed for oxygen delivery, it preferably has a second tube 24 which is intended to collect oxygen/carbon dioxide in the space of the vicinity of the patient's nose and mouth, and deliver that sample to an oxygen monitor (not illustrated) through tube 26. Tube 26 is releasably secured, during operation, within clip 12, for fluid communication with the corresponding oxygen/carbon dioxide monitor tube 24 of boom 14. Preferably tubes 23 and 24 are of integral construction. An appropriate oxygen/carbon dioxide inlet port 28 (FIG. 3) is associated with fastener 19 and diffuser 20, as will be described in more detail subsequently.

An optional means of securing boom 14 in position for oxygen delivery to a patient, instead of a headband, is a conventional over the ear mount 30 as shown in phantom in FIG. 1.

Figure 2:
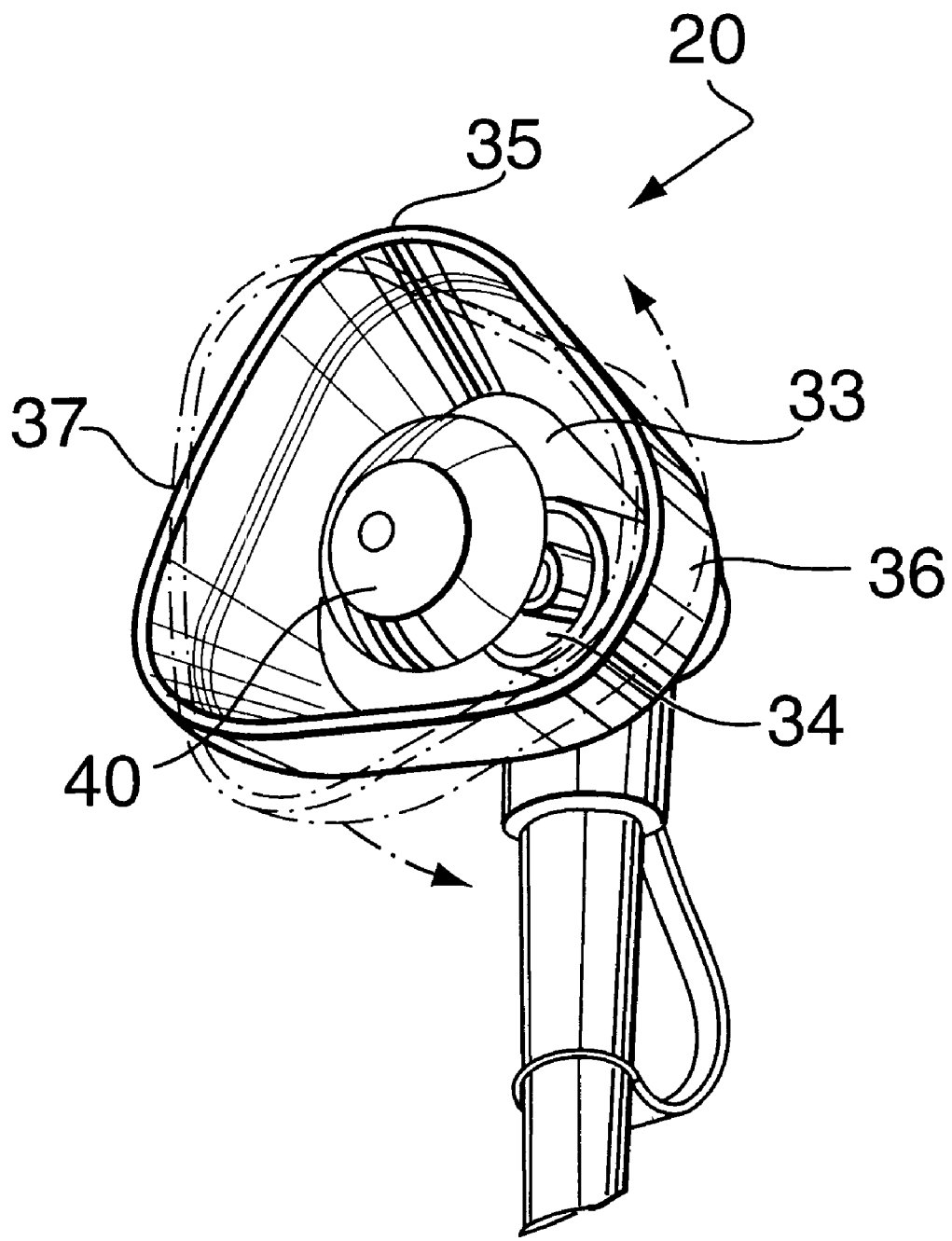
FIG. 2 is an enlarged perspective view of the diffuser of FIG. 1.
Figure 3:
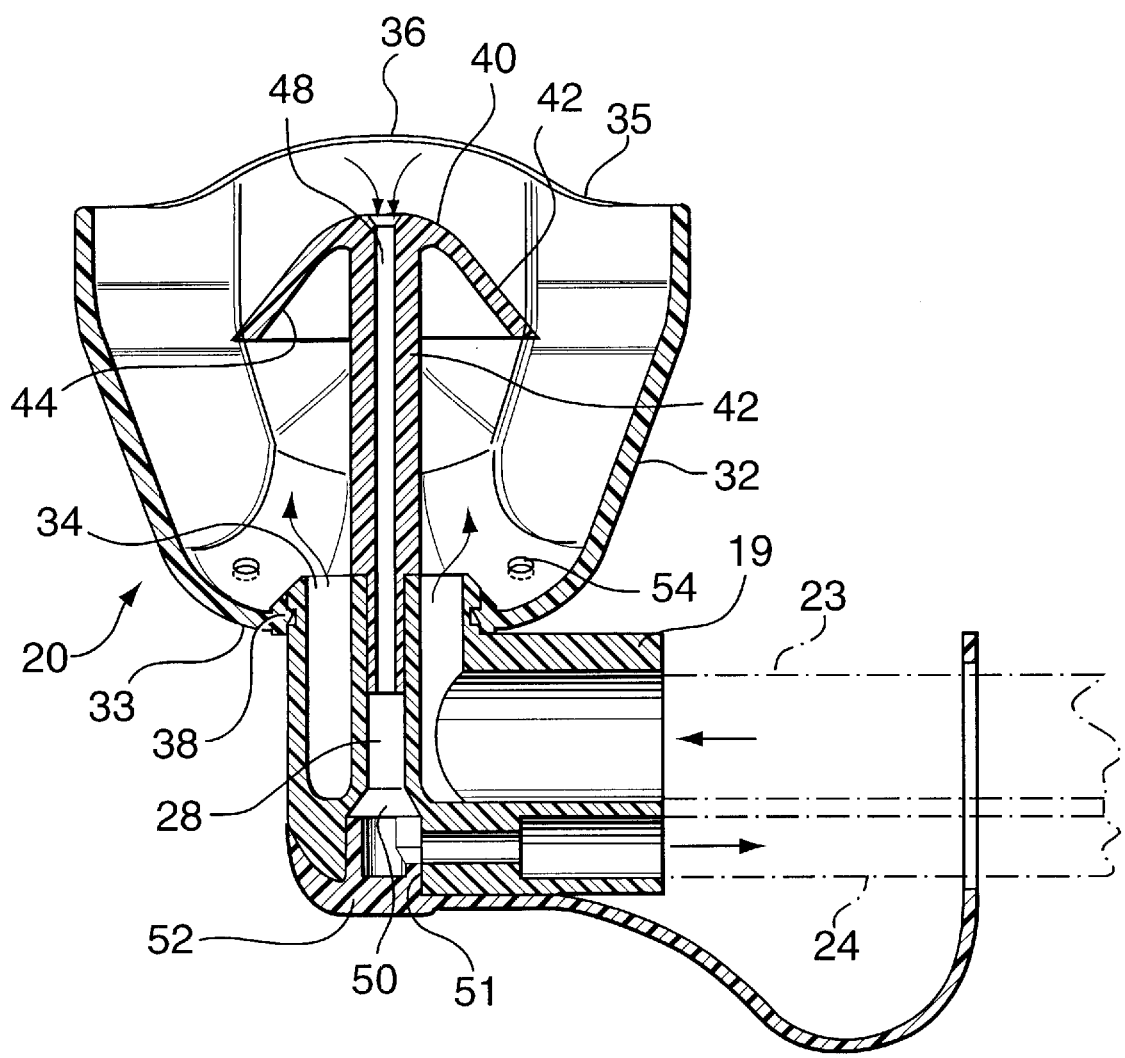
FIG. 3 is a section view of the diffuser of FIGS. 1 and 2.

The diffuser 20, detailed in perspective in FIG. 2 and in section in FIG. 3, has a body formed from a wall 32, of cup-shaped appearance, and extending from a base 33 where oxygen outlet 34 is positioned, outwardly and upwardly to an edge 35 of triangular peripheral contour. The peripheral corners are rounded, with one of the corners 36, intended to be the uppermost corner when in use, and the proximal portions of the wall edge, are raised with respect to the other corners and edge portions as illustrated to facilitate the direction of oxygen towards a patient's nose and mouth. This construction, with protruding corner 36 and proximal edges of the wall, being positioned proximal to the patient's nose when in use, and the wider triangular portion at the bottom proximal a patient's mouth, provides optimal oxygen delivery to a patient.

Because delivery system 2 is intended to be fully reversible, i.e. it may be worn on the left or right side, not only does the boom 14 rotate freely with respect to the headband 6 or earmount 30 but also diffuser 20 rotates, on fastener 19, 360 degrees about outlet port 34 by means of swivel 38.

Figure 4:
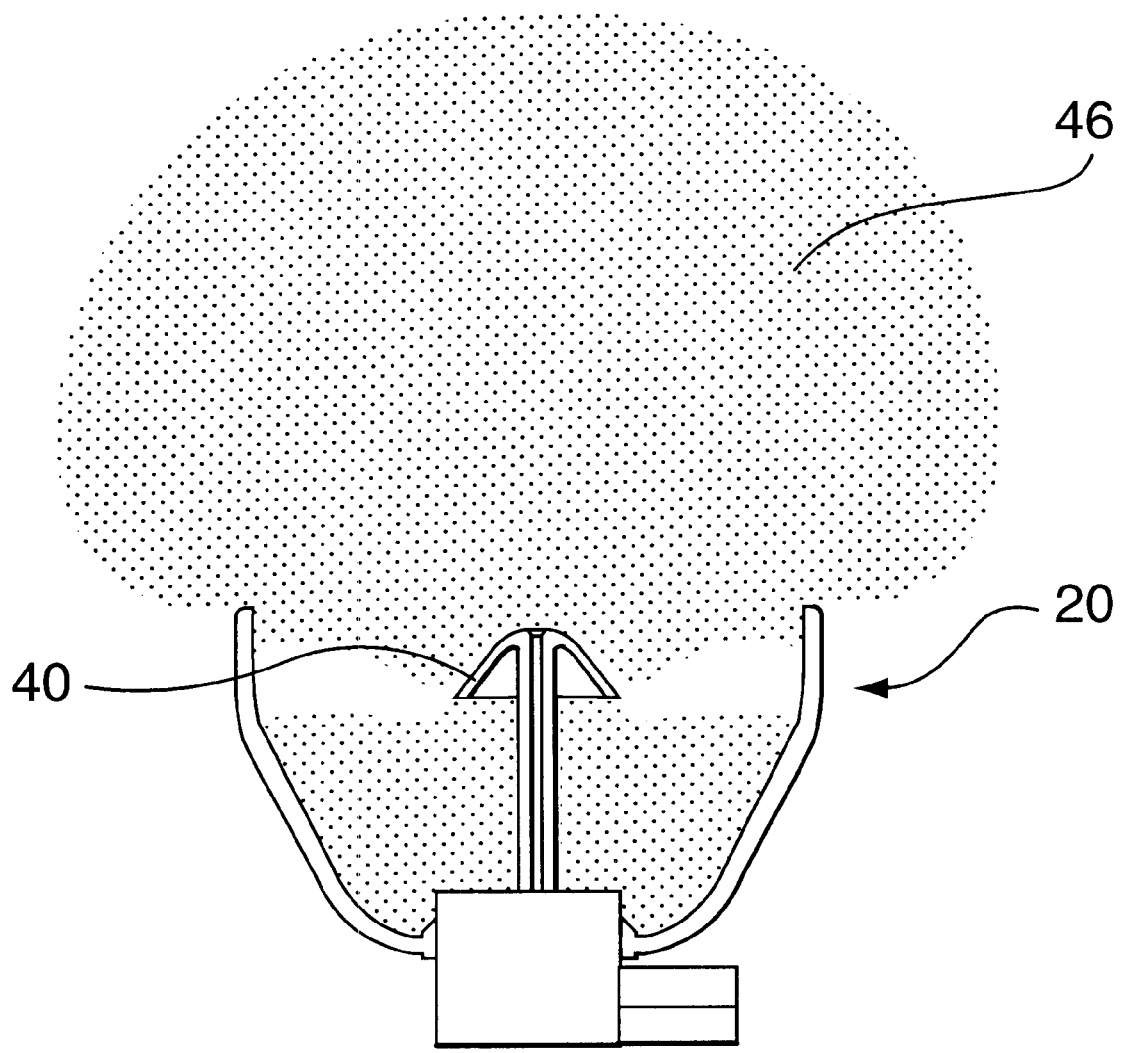
FIG. 4 is a schematic view, from the side, showing the plume of oxygen enriched air passed from the diffuser body during an operation of the system.

A mushroom-shaped baffle 40, having a central post 42 which is seated in and over oxygen outlet 34, is provided to assist in the diffusion of oxygen and avoid a direct flow of oxygen towards the patient's face. The upper end of baffle 40 has a curled-back lip 42 of conical shape so that oxygen flowing from outlet 34 is directed into an against the underside 44 of this lip, creating turbulence and mixing the pure oxygen with the ambient air. As can be seen in FIG. 4, a plume 46 of oxygen enriched air then leaves the diffuser, progressing towards the patient's nose and mouth area.

In other words, baffle 40 impedes oxygen flow directly from base 33, changing the oxygen transmission flow from ajet to a turbulent, plume-like flow.

Centrally located with post 42, extending from its bottom and through upper end 44, is a passageway 48 to permit gas analysis of expired gases from the patient. Passageway 48 provides a fluid communication from the environment in front of the patient's mouth and nose (when the delivery system is in operation) to the oxygen/carbon dioxide inlet port 28.

The enclosed volume of the cup-like body 32 of diffuser 20 may be modified to accommodate a larger plume and increase the total oxygen delivered during respiratory inspiration. The particular illustrated shaping of the walls and peripheral edges of the diffuser permits a concentrating of oxygen and a shaping of the plume 46, providing a more precise direction of the plume of oxygen towards the patient's nose/mouth.

As well, the overall shaping of body 32 and baffle 40 may be modified to suit the requirements of the particular application or user need.

Adding to the versatility of diffuser 20 is a vaporizer port 50 and channel 51 which passes through the back of fastener 19 and communicates with passageway 48 in baffle post 42, to permit feeding of a vaporizer dose (through a (not illustrated) tube inserted into channel 51 from a vaporizer source (again not illustrated)) to the patient through the diffuser. When vaporizer port 50 and channel 51 are thus in use, gas analysis through passageway 48 and tube 24 does not take place. A cap 52 seals vaporizer port 50 when this function is not required. The vaporizer dose is delivered through a tube (again not illustrated) with its delivery end releasably secured in vaporizer port 50.

It is also envisaged that a ridge or plurality of scented material holding pockets 54, in the surface of the diffuser body, may be provided for purposes of aromatherapy. Alternatively a layer of scented material may be coated on the inside surface of the wall 32 of diffuser 20.

Thus, it is apparent that there has been provided in accordance with the invention an oxygen diffuser for a lightweight oxygen delivery system that fully satisfies the objects, aims and advantages set forth above. While the invention has been described in conjunction with illustrated embodiments thereof, it is evident that many alternatives, modifications and variations will be apparent to those skilled in the art in light of the foregoing description. For example, a multi lumina boom 14, instead of one having a single or a pair of tubes, may be provided, each tube having a distinct function. Accordingly, it is intended to embrace all such alternatives, modifications and variations as fall within the spirit and broad scope of the invention.

What we claim as our invention:

1. An oxygen diffuser adapted for attachment to a lightweight oxygen delivery system for a patient, the oxygen delivery system comprising a mount for seated engagement on a patient's head or ear, an end of an elongated tubular boom for oxygen delivery secured to the mount and another end of the boom to which the diffuser is adapted to be secured, the diffuser to deliver oxygen passed through the boom to a space in the vicinity of the patient's nose and mouth, the diffuser comprising:
   a. a body having a wall with an interior surface of generally concave configuration, circumscribing a centrally positioned oxygen outlet opening into the concave interior surface so as to direct the flow of oxygen from the oxygen outlet generally towards the patient's nose and mouth, and
   b. a baffle including a post seated centrally within the oxygen outlet at one end with a curled-back conical lip at its other end and where an underside of the lip is located in a path of an oxygen stream exiting the oxygen outlet during operation of the diffuser so as generate turbulence to assist in mixing of oxygen with ambient air to create a mushroom-shaped plume of oxygen rich air proximate the patient's nose and mouth and avoiding a direct flow of oxygen towards the patient's face.

2. A diffuser according to claim 1 wherein a passageway is provided through the baffle, to communicate directly with an oxygen/carbon dioxide tube of the boom, in operation enabling a sample of oxygen or carbon dioxide, in the region of the patient's mouth and nose, to be drawn through this tube of the boom to an oxygen/carbon dioxide monitor.

3. A diffuser according to claim 2 further provided with a closable vaporizer port to permit feeding of a vaporizer dose from a vaporizer source to the patient through the diffuser.

4. A diffuser according to claim 2 wherein the passageway for oxygen/carbon dioxide monitoring passes centrally through the post.

5. A diffuser to claim 3 wherein the closable vaporizer port is associated with a channel constructed so that the vaporizer dose enters the diffuser through the port, and leaves the diffuser through the oxygen outlet.

6. A diffuser according to claim 5 further comprising a cap to sealable close the closable vaporizer port for the vaporizer dose.

7. A diffuser according to claim 1 wherein the wall is of cup-shaped configuration, extending from a base where the oxygen outlet is positioned, outwardly and upwardly to an edge of triangular peripheral contour.

8. A diffuser according to claim 7 wherein corners of the edge are rounded and one of the corners, intended when in use to be the uppermost corner, and portions of the wall edge proximal to said one of the corners are slightly raised with respect to the other corners and edge portions, to facilitate direction of oxygen towards a patient's nose.

9. A diffuser according to claim 8 wherein a diffuser is provided with a swivel adapted for attachment to the boom, whereby the diffuser may be rotated 360 degrees about the oxygen outlet when on the boom.

10. An oxygen diffuser for a lightweight oxygen delivery system for a patient, the oxygen delivery system comprising a mount for seated engagement on a patient's head or ear, an end of an elongated tubular boom for oxygen delivery secured to the mount and another end of the boom secured to the diffuser, the diffuser to delivery oxygen passed through the boom to a space in the vicinity of the patient's nose and mouth, the diffuser comprising:
   (a) a body having a wall with an interior surface of generally concave configuration, circumscribing a centrally positioned oxygen outlet opening into the concave interior surface so as to direct the flow of oxygen from the oxygen outlet generally towards the patient's nose and mouth,
   (b) a baffle seated over the oxygen outlet and located in a path of an oxygen stream exiting the oxygen outlet during operation of the diffuser so as to assist in mixing of oxygen with ambient air and avoid a direct flow of oxygen towards the patient's face; and
   (c) a closable vaporizer port to permit feeding of a vaporizer dose from a vaporizer source in the patient through the diffuser, the wall of the body being of a cup-shaped configuration, extending from a base where the oxygen outlet is positioned, outwardly and upwardly to an edge of triangular peripheral contour having three corners, the corners of the edge being rounded and one of the corners, intended when in use to be the uppermost corner, and portions of the edge proximal to said one of the corners, being slightly raised with respect to the other corners and edge portions, to facilitate direction of oxygen towards a patient's nose, and said diffuser being further provided with a swivel attachment to the boom, whereby the diffuser may be rotated 360 degrees on the boom, about the oxygen outlet.

* * * * *

UNITED STATES PATENT AND TRADEMARK OFFICE
CERTIFICATE OF CORRECTION

| | | |
|---|---|---|
| PATENT NO. | : 6,595,207 B1 | |
| APPLICATION NO. | : 09/659503 | |
| DATED | : July 22, 2003 | |
| INVENTOR(S) | : McDonald et al. | |

It is certified that error appears in the above-identified patent and that said Letters Patent is hereby corrected as shown below:

Column 6, lines 20-55, should be changed as follows:

10. An oxygen diffuser <u>adapted</u> for <u>attachment to</u> a lightweight oxygen delivery system for a patient, the oxygen delivery system comprising a mount for seated engagement on a patient's head or ear, an end of an elongated tubular boom for oxygen delivery secured to the mount and another end of the boom [secured to the diffuser] <u>to which the diffuser is adapted to be secured</u>, the diffuser to [delivery] <u>deliver</u> oxygen passed through the boom to a space in the vicinity of the patient's nose and mouth, the diffuser comprising:
     (a)     a body having a wall with an interior surface of generally concave configuration, circumscribing a centrally positioned oxygen outlet opening into the concave interior surface so as to direct the flow of oxygen from the oxygen outlet generally towards the patient's nose and mouth,
     (b)     a baffle seated over the oxygen outlet and located in a path of an oxygen stream exiting the oxygen outlet during operation of the diffuser so as to assist in mixing of oxygen with ambient air and avoid a direct flow of oxygen towards the patient's face; and
     (c)     a closable vaporizer port to permit feeding of a vaporizer dose from a vaporizer source in the patient through the diffuser, the wall of the body being of a cup-shaped configuration, extending from a base where the oxygen outlet is positioned, outwardly and upwardly to an edge of triangular peripheral contour having three corners, the corners of the edge being rounded and one of the corners, intended when in use to be the uppermost corner, and portions of the edge proximal to said one of the corners, being slightly raised with respect to the other corners and edge portions, to facilitate direction of oxygen towards a patient's nose, and said diffuser being further provided with a swivel <u>adapted for</u> attachment to the boom, whereby the diffuser may

UNITED STATES PATENT AND TRADEMARK OFFICE
CERTIFICATE OF CORRECTION

PATENT NO. : 6,595,207 B1
APPLICATION NO. : 09/659503
DATED : July 22, 2003
INVENTOR(S) : McDonald et al.

It is certified that error appears in the above-identified patent and that said Letters Patent is hereby corrected as shown below:

be rotated 360 degrees on the boom, about the oxygen outlet.

Signed and Sealed this

Twenty-first Day of July, 2009

JOHN DOLL
*Acting Director of the United States Patent and Trademark Office*